United States Patent
Hirota

(10) Patent No.: US 6,437,168 B1
(45) Date of Patent: Aug. 20, 2002

(54) METHOD FOR PRODUCTION OF AROMATIC FLUORINE COMPOUND

(75) Inventor: Kouichi Hirota, Kobe (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/941,826

(22) Filed: Aug. 29, 2001

(30) Foreign Application Priority Data

Sep. 5, 2000 (JP) ........................................ 2000-268454

(51) Int. Cl.[7] ........................ C07C 255/00; C07C 17/38
(52) U.S. Cl. ........................ 558/425; 570/147; 570/177; 570/180
(58) Field of Search ................................ 570/147, 177, 570/180; 558/425

(56) References Cited

U.S. PATENT DOCUMENTS

| 4,684,734 A | | 8/1987 | Kaieda et al. ............... 546/345 |
| 5,315,043 A | * | 5/1994 | Fernandez et al. ........... 570/166 |
| 6,241,917 B1 | | 6/2001 | Owens et al. ............ 260/665 G |
| 6,265,627 B1 | | 7/2001 | Igumnov et al. ............ 570/147 |

FOREIGN PATENT DOCUMENTS

| EP | 1 097 914 A2 | 5/2001 | ........... C07B/39/00 |
| GB | 2 142 018 | 1/1985 | ......... C07C/255/50 |
| JP | 62-7185 | 2/1987 | ......... C07C/121/52 |
| JP | 1-49346 | 10/1989 | ......... C07C/121/56 |
| JP | 2-16746 | 4/1990 | ......... C07C/255/50 |
| JP | 4-4309 | 1/1992 | ......... C07C/255/51 |
| WO | WO 98/22413 | 5/1998 | ........... C07C/17/20 |
| WO | WO 99/40052 | 8/1999 | ........... C07C/17/38 |

* cited by examiner

Primary Examiner—Alan Siegel
(74) Attorney, Agent, or Firm—Fish & Richardson P.C.

(57) ABSTRACT

A method for efficiently extracting a reaction product containing a target aromatic fluorine compound formed by the halogen exchange reaction of an aromatic chlorine compound with a fluorinating agent quickly from the reaction vessel without suffering part of the reaction product to remain as a residue inside the reaction vessel is disclosed. Specifically, the reaction product is extracted from the reactor subsequently to the halogen exchange reaction at a temperature in the range of 20–250° C. By this method, the reaction product formed in consequence of the halogen exchange reaction can be efficiently extracted quickly from the reaction vessel, and that without suffering occurrence of a residue of the reaction product.

15 Claims, No Drawings

METHOD FOR PRODUCTION OF AROMATIC FLUORINE COMPOUND

BACKGROUND OF THE INVENTION

1. Field of the Invention

This invention relates to a method for the production of an aromatic fluorine compound, and more particularly to a method for extracting a reaction product containing a target aromatic fluorine compound formed by the halogen exchange reaction of an aromatic chlorine compound with a fluorinating agent efficiently from the reaction vessel.

2. Description of Related Art

The method for producing an aromatic fluorine compound by the halogen exchange reaction of an aromatic chlorine compound with a fluorinating agent is well known method. The official gazette of JP-B-62-7,185, for example, described a method for obtaining pentafluorobenzonitrile by subjecting pentachlorobenzonitrile and a fluorinating agent to the halogen exchange reaction in benzonitrile. A working example, recommending a reaction temperature in the range of 270–400° C. and a reaction time in the range of 2–48 hours, obtained a target product by charging an autoclave with benzonitrile, pentachlorobenzonitrile, and dry potassium fluoride and then heating and stirring the components at 320° C. for 16 hours therein. After completion of the reaction, the reaction solution was treated by the use of a rotary evaporator at an ambient temperature of 200° C. to separate potassium chloride and unaltered potassium fluorine from the solution and obtain on the bottom of the kettle a benzonitrile solution containing pentafluorobenzonitrile.

The official gazette of JP-B-01-49,346 discloses a method for obtaining tetrafluorophthalonitrile by subjecting tetrachlorophthalonitrile and a fluorinating agent to a halogen exchange reaction in benzonitrile. A working example, recommending a reaction temperature in the range of 190–320° C. and a reaction time in the range of 2–48 hours, obtained a target product by charging an autoclave with benzonitrile, tetrachlorophthalonitrile, and dry potassium fluoride and then heating and stirring these components at 255° C. for 16 hours therein. After completion of the reaction, the reaction solution was treated by the use of a rotary evaporator at an ambient temperature of 230° C. to separate potassium chloride and unaltered potassium fluoride from the solution and then the separated solution was distilled to obtain benzonitrile and tetrafluorophthalonitrile by evaporation.

Then, the official gazette of JP-B-02-16,746 discloses a method for effecting the halogen exchange reaction in a non-protone polar solvent or in the absence of a solvent. A working example, recommending a reaction temperature in the range of 200–450° C. and a reaction time in the range of 0.5–30 hours, obtained the target product by charging an autoclave with 2,6-dichlorobenzonitrile and potassium fluoride and heating these components at 350° C. for three hours for the purpose of inducing the components to react. After completion of the reaction, the reaction product was cooled and, from the neighborhood of 200° C. downward, treated by the use of a distilling device to obtain the target product.

The official gazette of JP-B-04-4,309, discloses a method for inducing 3,4,5,6-tetrachlorophthalonitrile to undergo a reaction in the presence of a benzonitrile solvent by heating the reaction mixture under a spontaneously generated pressure or under normal pressure while keeping the mixture in a refluxed state. A working example, recommending a reaction temperature in the range of 190–400° C. and a reaction time in the range of 4–48 hours with a view to preventing the solubility of potassium fluoride from abruptly rising in consequence of the use of benzonitrile at a temperature exceeding the boiling point thereof, obtained a target product by charging an autoclave with 3,4,5,6-tetrachlorophthalonitrile and dry potassium fluoride and heating the components at 230° C. for 10 hours for the purpose of inducing these components to react. After completion of the reaction, the reaction product was cooled to room temperature and the consequently suspended potassium chloride and the unaltered potassium fluoride were removed by filtration, with the result that the target product, i.e. 3,4,5,6-tetrafluorophthanlonitrile, was obtained in the filtrate. The methods disclosed in the official gazettes mentioned above invariably adopted a procedure of charging a reaction vessel with relevant raw material compounds, synthesizing a target product therein, extracting the product from the reaction vessel, and refining the target product in a separate vessel furnished with a filtering device or an evaporator.

The fluorinating agent which fulfills the role of inducing an aromatic chlorine compound and a fluorinating agent to undergo a halogen exchange reaction, however, is suffered to remain as a precipitate in the reaction solution occurring after completion of the halogen exchange reaction because it is the fluoride salt of an alkali metal such as cesium fluoride, potassium fluoride, or sodium fluoride or the fluoride salt of an alkaline earth metal such as barium fluoride or calcium fluoride. Since the reaction product formed by the halogen exchange reaction generally is a slurry of high viscosity, it is at a disadvantage in requiring an unduly long time for the work of extraction thereof from the reaction vessel and suffering part of the reaction product to remain as a residue in the reaction vessel. Since the raw material compounds and the target product generally emit a strong odor, it is practically difficult for the worker to collect the reaction product directly from the interior of the reaction vessel by reason of labor hygiene. Particularly, the process of the reaction mentioned above possibly by-produces hydrogen fluoride which is a corrosive compound. In the halogen exchange reaction which is carried out more often than not in a batchwise mode, therefore, it is an immensely important task to accomplish the extraction of the reaction product efficiently from the reaction vessel fresh from the completion of the target product without entailing leakage of the odor in the ambience and without exposing the worker to the atmosphere of the reaction product mentioned above.

In the fields of production, therefore, the desirability of developing a method for quickly extracting the reaction product from the reaction vessel, and that without suffering part thereof to remain as a residue inside the reaction vessel, has been finding enthusiastic recognition.

SUMMARY OF THE INVENTION

The object implied above is accomplished by the following invention.

(1) A method for the production of an aromatic fluorine compound by the halogen exchange reaction of an aromatic chlorine compound with a fluorinating agent, characterized by extracting the aromatic fluorine compound obtained by the halogen exchange reaction from a reaction vessel at a temperature in the range of 20–250° C.

This invention enables the reaction product fresh from the completion of the halogen exchange reaction to be efficiently extracted quickly from the reaction vessel without suffering part thereof to remain as a residue therein.

DETAILED DESCRIPTION OF THE PREFERRED EMBODIMENTS

This invention is directed, a method for the production of an aromatic fluorine compound by the halogen exchange reaction of an aromatic chlorine compound with a fluorinating agent, characterized by extracting the aromatic fluorine compound obtained by the halogen exchange reaction from a reaction vessel at a temperature in the range of 20–250° C.

The term "aromatic chlorine compound" as used in this invention refers to a compound containing at least one chlorine atom in an aromatic ring thereof. It means a compound which may be possessed of a substituent other than chlorine atom such as, for example, an electron attractive substituent such as cyano group, nitro group, or fluorocarbonyl group besides the chlorine atom. As concrete examples of the aromatic chlorine compound, the compounds represented by the following general formula (1) and (2) may be cited.

General formula (1)

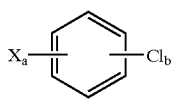

(wherein Cl denotes a chlorine atom, —X denotes any member selected from the element consisting of —CN, —NO$_2$, —COF, and —COCl, a denotes the number of substitutions of X, i.e. 0, 1, or 2, b denotes the number of substitutions of chlorine atom satisfying the formula b≧1, providing that the sum of a and b satisfy the formula a+b<6, and, in the occurrence of a plurality of X's, the individual X's may be the same or different.)

General formula (2)

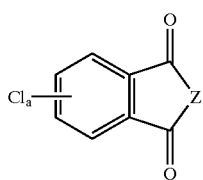

(wherein Cl denotes a chlorine atom, —Z— denotes —O— or >NR (wherein R denotes a hydrogen atom, an alkyl group of 1–6 carbon atoms, or an aryl group), a denotes the number of substitutions of chlorine atom, i.e. an integer satisfying the formula 1<a<4. )

As typical examples of the compounds represented by the general formulas (1) and (2) mentioned above, monochlorobenzene, dichlorobenzene, trichlorobenzene, tetrachlorobenzene, pentachlorobenzene, hexachlorobenzene, 2,6-dichlorobenzonitrile, 2,4,6-trichlorobenzonitrile, pentachlorobenzonitrile, 3,4,5,6-tetrachlorophthalonitrile, tetrachlorophthalic anhydride, tetrachlorophthalic acid difluoride, tetrachlorophthalic anhydride amide, N-alkyltetrachlorophthalic anhydric amide (the alkyl group: methyl, ethyl, n-propyl, isopropyl, n-butyl, isobutyl, etc.), N-phenyltetrachlorophthalic anhydride amide, 2,3,4-trichloronitrobenzene, and pentachloronitrobenzene may be cited. Among other compounds enumerated above, 3,4,5,6-tetrachlorophthalonitrile, pentachlorobenzonitrile, and 2,6-dichlorobenzonitrile are particularly advantageously used.

The halogen exchange reaction may be carried out in the presence of an organic solvent or in the absence of a solvent. As organic solvents, such so-called non-protone polar solvents as dimethyl sulfoxide (DMSO), sulfolane (TMSO$_2$), N,N-dimethyl sulfoxide (DMF), N-methyl-2-pyrrolidone (NMP), and dimethyl sulfone ((DMSO$_2$) or benzonitrile are generally used. From the view point of reactivity and thermal stability, benzonitrile is particularly advantageously used.

The fluorinating agent may be any of such fluorinating agents as are usable for the halogen (fluorine) exchange reaction with the aromatic chlorine compound. Such alkali metal fluorides as sodium fluoride, potassium fluoride, and cesium fluorine are used advantageously and potassium fluoride is used particularly advantageously. The amount of the fluorinating agent must be at least equimolar to the chlorine atoms contained in the aromatic chlorine compound in the raw material compounds which are substituted for by fluorine atoms. Generally, the fluorinating agent is used in an amount such that it contains 1.0–1.5 fluorine atoms per chlorine atom.

The halogen exchange does not need to be particularly discriminated but may be effected in accordance with any of the methods generally used for this kind of reaction. It may be carried out in the absence of a solvent as disclosed in the official gazette of JP-B-02-16,746, to the accompaniment of the circulation of an organic solvent containing an unaltered mixture obtained from the bottom of a distilling column as disclosed in the official gazette of JP-B-62-7,185, or in compliance with a series of steps of adding raw material compounds into a benzonitrille solvent and refluxing the resultant solution at a temperature in the range of 190–400° C. under a spontaneously generated pressure or under normal pressure until the components are induced to react as disclosed in the official gazette of JP-B-04-4,309. Generally, this reaction is effected by stirring the raw materials in a pressureproof reaction vessel formed of such a chemical-resistant material as SUS 316 and provided with an agitation element.

The method of this invention is satisfactorily used in performing a halogen exchange reaction of 2,6-dichlorobenzonitrile, tetrachlorophthalonitrile, or pentachlorobenzonitrile with a fluorinating agent in the absence of a solvent or preferably in the presence of such a solvent as a non-protone polar solvent or benzonitrile and then extracting the resultant reaction product from the reaction vessel.

The reaction product obtained by the halogen exchange reaction possesses high viscosity and occasionally manifests thixotropy because it contains such an inorganic salt as potassium chloride formed by the reaction in addition to the aromatic fluorine compound as the target product. Frequently, therefore, it is not easily extracted smoothly from the reaction vessel. By the method of this invention, however, the reaction product of such quality is enabled to be extracted quickly from the reaction vessel without suffering occurrence of a residue in the reaction vessel.

This invention is characterized by extracting the reaction product mentioned above from the reaction vessel at a temperature in the range of 20–250° C. The aromatic fluorine compound which is the target of production is generally shifted subsequently to completion of the halogen exchange reaction to the next step and subjected therein to purification of the target product. For the purpose of this purification, the practice of allowing the reaction product to stand at rest and then treated at a low temperature is generally adopted because the product has caustic property. In this case, the reaction possibly suffers the by-produced potassium chloride and the residual excess potassium fluoride to solidify and the solid consequently formed entails such problems as blocking the outlet port during the extraction of the reaction product and rendering the extraction difficult. The blockage so caused by the reaction product has been heretofore eliminated by the practice of inserting an extracting tool into the reaction vessel and manipulating this tool so as to rake out the content of the reaction vessel or injecting a solvent into the reaction vessel and using the solvent so as to solve the solidified reaction product. This invention, owing to the discovery that the necessary fluidity of the reaction product can be secured by adjusting the temperature of the reaction product at the time of extraction in the range of 20–250° C., enables the extraction of the reaction product to be immensely facilitated.

In accordance with this invention, the reaction product is extracted from the reaction vessel at a temperature in the range of 20–250° C., preferably in the range of 50–230° C., more preferably in the range of 100–220 and especially in the range of 150–200° C. If this temperature falls short of 20° C., the shortage will be at an economic disadvantage in raising the viscosity of the reaction product, disabling smooth extraction of the reaction product, and requiring an extra time for cooling the reaction product to below 20° C. Conversely, if the temperature exceeds 250° C., the excess will be at an economic disadvantage in causing the target product or the solvent to be transformed into a vaporized state on the extraction vessel side owing to the high temperature of the reaction product at the time of extraction, consequently suffering the vaporized components to fly in all directions, and inevitably compelling the components thus in flight to entrain the inorganic salt present in the reaction product and defile the devices disposed nearby.

This invention, by keeping the reaction product stirred and simultaneously adjusting the temperature of the reaction product in the range of 20–250° C., enables the reaction product to secure still better fluidity. Particularly, since the aromatic fluorine compound which is the target product of this invention uses a fluorinating agent which belongs to the class of inorganic compounds, it is generally proper to stir the reaction product with stirring power per unit volume of the reaction product in the range of 0.1–10 kw/m$^3$, preferably in the range of 0.5–7.0 kw/m$^3$, and particularly preferably in the range of 1.0–4.0 kw/m$^3$ for the purpose of securing the reactivity with the fluorinating agent at the time of reaction. It has been heretofore customary to stop the stirring after completion of the reaction. This invention, by continuing the stirring simultaneously with the control of temperature mentioned above, enables the reaction product to secure the necessary fluidity. The stirring power during the temperature control may be the same or different from the stirring power during the course of the reaction. The stirring power per unit volume of the reaction product is in the range of 0.1–10 kw/m$^3$, preferably in the range of 0.5–7.0 kw/m$^3$, and particularly preferably in the range of 1.0–4.0 kw/m$^3$. The stirring power during the extraction of the reaction product from the reaction vessel as reduced to the stirring power per unit volume of the reaction product is in the range of 0.01–3.0 kw/m$^3$, preferably in the range of 0.05–2.5 kw/m$^3$, and particularly preferably in the range of 0.1–2 kw/m$^3$. The reason for this particular range is that the fluidity of the reaction product which is proper for the extraction from the reaction vessel can be secured in this range no matter whether the reaction product contains a solvent and without reference to the amount of the fluorinating agent to be incorporated. Not only during the temperature control but also during the extraction of the reaction product, the reaction product may be extracted by rotating the agitation element.

The stirring power per unit volume of the reaction product during the course of extraction as contemplated by this invention is found by calculating necessary stirring powers from the magnitudes of electric current of the stirring device before and after the extraction, deriving the necessary stirring power from the difference between the two magnitudes, and dividing this necessary stirring power by the volume of the reaction product. Specifically, since the stirring power (A) during the course of the reaction or during the cooling of the reaction product (prior to the extraction) is expressed by the formula, ($\sqrt{3}\times$ AC voltage$\times$magnitude 1 of electric current$\times$power factor 1)/1000, and the stirring power (B) during the collection of the extracted reaction product (at completion of the extraction) is expressed by the formula, ($\sqrt{3}\times$ AC voltage$\times$magnitude 2 of electric current$\times$power factor 2)/1000, the stirring power per unit volume of the reaction product during the course of the extraction will be expressed by the formula, [(a)–(B)]/volume of the reaction product. As implied by the numerical value, the stirring power during the course of extraction indicates the average stirring power over the time elapsing during the extraction of the reaction product. In this case, by performing the extraction of the reaction product under pressure or by effecting the extraction of the reaction product by virtue of the suction exerted on the reaction product. Specifically, by allowing the internal pressure of the reaction vessel to surpass the external pressure thereof or, in the case of an apparatus comprising a reaction vessel and a container connected thereto for receiving the reaction product, for example, by allowing the internal pressure of the reaction vessel to surpass the internal pressure of the container for receiving the reaction product, it is made possible to extract the reaction product efficiently from the reaction vessel.

Various methods may be relied on to enable the internal pressure of the reaction vessel to surpass the outer pressure. This relationship of pressure, for example, may be established by forcing a gas into the reaction vessel during the extraction of the reaction product or by decompressing the internal pressure of the container connected to the reaction vessel for receiving the reaction product by the use of a pump. The degree of this decompression varies with the viscosity of the reaction product. When the viscosity of the reaction product measured with a BL type viscosimeter (made by Tokimeck K.K.) is in the range of 2–200 cps, it suffices to make the pressure on the reaction side surpass the internal pressure of the container for receiving the reaction product by a difference in the range of 0.01–2 MPa, preferably in the range of 0.05–1 MPa, and more preferably in the range of 0.1–0.5 Mpa as gauge pressure. For the generation of the pressure difference mentioned above, the method which relies on the introduction of a gas into the reaction vessel is used fully satisfactorily in the sense that it is comparatively easy to operate and capable of generating a pressure difference of not less than 0.1 MPa.

The gas to be used in this case does not need to be particularly discriminated but is only required to warrant safe use on a commercial scale. As concrete examples of the gas answering the description, inert gases such as nitrogen, carbon dioxide, helium, and argon, and air, and the air having a lowered oxygen concentration may be cited. Among other gases mentioned above, nitrogen is favorably used because it is incapable of adversely affecting the reaction product, safe, and readily available commercially.

As means for effecting the extraction of the reaction product, a method which comprises using atmospheric pressure for the internal pressure of the reaction vessel, imparting a decompressed state by the use of a pump to the interior of the container for receiving the reaction product, and extracting the reaction product while keeping the reaction product in a stirred state or not in a stirred state may be cited in addition to a method which comprises imparting a depressed state with using an inert such gas as nitrogen, to the interior of the reaction vessel and effecting the extraction while keeping the reaction product in a stirred state or not in a stirred state. The method which relies on the action of stirring to effect the extraction is preferred over the other method because it is capable of extracting the reaction product more smoothly and efficiently. The inert gas like nitrogen which discharges the role of imparting a pressed state to the interior of the reaction vessel is preferred to be suitably supplied into the reaction vessel while the state of extraction or the internal pressure of the extraction vessel is kept under observation so as to smooth the extraction. Incidentally, when a small amount of the reaction product happens to remain as a residue in the reaction vessel, the removal of this residue maybe attained, for example, by introducing a solvent into the reaction vessel, stirring the solvent together with the residue until a slurry of satisfactory state is formed, and thereafter removing the slurry out of the reaction vessel.

The reaction product obtained by the method has high viscosity because inorganic salts such as the potassium chloride by-produced by the reaction, the residual unaltered fluorinating agent persist as insoluble components and the aromatic chlorine compound as the raw material compound in the reaction product. Particularly, when the number of chlorine atoms contained in the aromatic chlorine compound is large, the reaction product acquires proportionately higher viscosity because the amount of the fluorinating agent to be used is naturally increased and the amount of the by-produced potassium chloride or the unaltered fluorinating agent remaining in the reaction product is consequently increased. From this point of view, the method for production according to this invention is particularly effective when such an aromatic chlorine compound as 3,4,5,6-tetrachlorophthalonitrile or pentachlorobenzonitrile which has 4 or 5 chlorine atoms in one compound is used as the raw material compound. When 2,6-dichlorobenzonitrile is used as a raw material, the reaction product acquires higher viscosity because the reaction thereof with the fluorinating agent is possibly effected in the absence of a solvent in spite of the small number of chlorine atoms to be contained therein. When 2,6-dichlorobenzonitrile is adopted as a raw material compound, therefore, this invention enables the reaction product to be extracted fully satisfactorily even when the halogenation reaction is carried out in the absence of a solvent.

EXAMPLES

Now, this invention will be described more specifically below with reference to working examples to be cited herein below.

Referential Example 1

In an autoclave measuring 300 liters in inner volume and made of stainless steel, 150 kg of benzonitrile, 52 kg (189.1 mols) of pentachlorobenzonitrile, and 60 kg (1033 mols of spray dried potassium fluoride were placed and, after displacement of the air remaining in the autoclave with nitrogen, were heated at 340° C. for 18 hours as kept stirred with stirring power per unit volume of the reaction product in the range of 1.0–3.0 kw/m³ until the components were induced to react.

When the reaction solution was analyzed by gas chromatography after completion of the reaction, it was found to contain 31.1 kg (161.2 mols, yield 85.4 mol %), the target product, and 8.2 kg (39.1 mols) of 3,5-dichloro-2,4,6-trifluorobenzonitrile, an effective component).

Example 1

In an autoclave measuring 300 liters in inner volume and made of stainless steel, 150 kg of benzonitrile, 52 kg (189.1 mols) of pentachlorobenzonitrile, and 60 kg (1033 mols) of spray dried potassium fluoride were placed and, after displacement of the air remaining in the autoclave with nitrogen, were heated at 340° C. for 18 hours as kept stirred with stirring power in the range of 1.0–3.0 kw/m³ until the components were induced to react.

After the reaction was completed, the reaction solution was cooled to 150° C. as stirred with stirring power in the range of 1.0–3.0 kw/m³, the interior of the reaction vessel was pressed to 0.3 MPa with nitrogen gas as kept in a stirred state, and the valve in the lower part of the reaction vessel was opened so as to extract the reaction vessel to a blender connected to the valve in the lower part of the reaction vessel. The stirring power per unit volume of the reaction product at the time of extraction computed from the magnitudes of electric current of the drive part of the stirring device before and after the extraction was 0.4 kw/m³. The time required for the extraction was 5 minutes.

When the extracted reaction product was analyzed by gas chromatography, it was found to contain 30.8 kg (159.6 mols, yield 85.0 mol %), the target product, and 8.1 kg (35.8 mols) of 3,5-dichloro-2,4,6-trifluorobenzonitrile, an effective component. When the interior of the reaction vessel was visually inspected, it showed practically no presence of a residue of the reaction product. The recovery percentage (the recovery percentage after the extraction based on the yield of Referential Example 1; which applies similarly hereinafter) was 99%.

Example 2

In an autoclave measuring 300 liters in inner volume and made of stainless steel, 150 kg of benzonitrile, 52 kg (195.5 mols) of tetrachlorophthalonitrile, and 50 kg (860.1 mols) of spray dried potassium fluoride were placed and, after displacement of the air remaining in the autoclave with nitrogen, were heated at 255° C. for 20 hours as kept stirred with stirring power in the range of 1.0–3.0 kw/m³ until the components were induced to react.

After the reaction was completed, the reaction solution was cooled to 150° C. as stirred with stirring power in the range of 1.0–3.0 kw/m³, the interior of the reaction vessel was pressed to 0.3 MPa with nitrogen gas as kept in a stirred state, and the valve in the lower part of the reaction vessel was opened so as to extract the reaction vessel to a blender connected to the valve in the lower part of the reaction vessel. The stirring power per unit volume of the reaction product at the time of extraction computed from the magnitudes of electric current of the drive part of the stirring device before and after the extraction was 0.45 kw/m³. The time required for the extraction was 4 minutes. When the extracted reaction product was analyzed by gas chromatography, it was found to contain 35.2 kg (176.0 mols, yield 90.0 mol %), the target product, and 2.54 kg (11.7 mols) of 3-chloro-4,5,6-trifluorophthalonitrile, an effective component. When the interior of the reaction vessel was visually inspected, it showed practically no presence of a residue of the reaction product. The recovery percentage was 99%.

Example 3

In an autoclave measuring 300 liters in inner volume and made of stainless steel, 150 kg of dimethyl sulfoxide, 52 kg (302.3 mols) of 2,6-dichlorobenzonitrile, and 38.6 kg (665.1 mols) of spray dried potassium fluoride were placed and, after displacement of the air remaining in the autoclave with nitrogen, were heated at 160° C. for 12 hours as kept stirred with stirring force in the range of 1.0–3.0 kw/m³ until the components were induced to react.

After the reaction was completed, the reaction solution was cooled to 150° C. as stirred with stirring power in the range of 1.0–3.0 kw/m³, the interior of the reaction vessel was pressed to 0.2 MPa with nitrogen gas as kept in a stirred state, and the valve in the lower part of the reaction vessel was opened so as to extract the reaction vessel to a blender connected to the valve in the lower part of the reaction vessel. The stirring power per unit volume of the reaction product at the time of extraction computed from the magnitudes of electric current of the drive part of the stirring device before and after the extraction was 0.38 kw/m³. The time required for the extraction was 4 minutes. When the extracted reaction product was analyzed by gas chromatography, it was found to contain 38.8 kg (279.0 mols, yield 92.3 mol %), the target product, and 2.12 kg (13.6 mols) of 2-chloro-6-fluorobenzonitrile, an effective component. When the interior of the reaction vessel was visually inspected, it showed practically no presence of a residue of the reaction product. The recovery percentage was 99%.

Example 4

The extraction of a reaction-product was effected by following the procedure of Example 1 while changing the temperature of the reaction product at the time of extraction to 100° C. The time required for the extraction was 7 minutes. The recovery percentage was 98.5%.

Example 5

The extraction of a reaction product was effected by following the procedure of Example 1 while changing the internal pressure of the reaction vessel at the time of extraction to 0.5 MPa. The time required for the extraction was 3 minutes. The recovery percentage was 99.5%.

Example 6

The extraction of a reaction product was effected by following the procedure of Example 1 while changing the temperature of the reaction product at the time of extraction to 150° C. and changing the pressure on the extraction vessel side to 0.013 MPa by the use of a pump. The time required for the extraction was 6 minutes. The recovery percentage was 99.0%.

Comparative Example 1

The extraction of a reaction product was effected by following the procedure of Example 1 while changing the temperature of the reaction product at the time of extraction to 10° C. The time required for the extraction was 60 minutes. The recovery percentage was 70.0%.

Comparative Example 2

The extraction of a reaction product was effected by following the procedure of Example 1 while changing the temperature of the reaction product at the time of extraction to 28020 C. The time required for the extraction was 3 minutes. The recovery percentage was 80%.

Example 7

In an autoclave measuring 300 liters in inner volume and made of stainless steel, 150 kg of benzonitrile, 50 kg of pentachlorobenzonitrile, and 58 kg of spray dried potassium fluoride were placed and, after displacement of the air remaining in the autoclave with nitrogen, were heated to 340° C. and kept at this temperature for 18 hours as kept stirred with stirring power in the range of 2.0–4.0 kw/m³ until the components were induced to react. After the reaction was completed, the reaction solution was cooled to 190° C. as stirred with stirring power in the range of 2.0–4.0 kw/m³, the interior of the reaction vessel was pressed to 0.3 MPa with nitrogen gas as kept in a stirred state, and the valve in the lower part of the reaction vessel was opened so as to extract the reaction product to a blender connected to the valve in the lower part of the reaction vessel. The stirring power per unit volume of the reaction product at the time of extraction computed from the magnitudes of electric current of the drive part of the stirring device before and after the extraction was 0.5 kw/m³. The time required for the extraction was 1 minute. When the extracted reaction product was analyzed by gas chromatography, it was found to contain 32.8 kg (yield 93.7 mol %), the target product, 1.9 kg of 3-chloro-2,4,5,6-tetrafluorobenzonitrile, an effective component, and 0.4 kg of 3,5-dichloro-2,4,6-trifluorobenzonitrile. When the interior of the reaction vessel was visually inspected, it showed practically no presence of a residue of the reaction product. The recovery percentage was 99.8%.

Example 8

The extraction of a reaction product was effected by following the procedure of Example 7 while changing the temperature of extraction to 230° C. and changing the stirring power per unit volume of the reaction product to 0.4 kw/m³. The time required for the extraction was 8 minute. The recovery percentage was 95%.

Example 9

The extraction of a reaction product was effected by following the procedure of Example 7 while changing the temperature of extraction to 50° C. The time required for the extraction was 7 minutes. The recovery percentage was 96%.

Example 10

In a glass-lined reaction vessel measuring 300 liters in inner volume and provided with a stirring device and a condenser, 150 kg of sulfolane, 58 kg (194 mol) of N-methyl-tetrachlorophthal amide, and 50 kg of spray dried potassium fluoride were placed and, after displacement of the air remaining in the reaction vessel with nitrogen, were heated to 220° C. as stirred with stirring power in the range of 2.0–4.0 kw/m³ and retained at this temperature for 5 hours for the purpose of inducing the components to react. After the reaction was completed, the reaction solution was cooled to 190° C. as stirred with stirring power in the range of 2.0–4.0 kw/m³, the interior of the reaction vessel was pressed to 0.05 MPa with nitrogen gas as kept in a stirred state, and the valve in the lower part of the reaction vessel was opened so as to extract the reaction product through the valve in the lower part of the reaction vessel to a blender connected to the valve in the lower part of the reaction vessel. The stirring power per unit volume of the reaction product at the time of extraction computed from the magnitudes of electric current of the drive part of the stirring device before and after the extraction was 0.48 kw/m³. The time required for the extraction was 2 minutes. When the extracted reaction product was analyzed by gas chromatography, it was found to contain 37 kg (158.9 mols, yield 81.9 mol %), the target product. The interior of the reaction vessel showed practically no presence of a residue of the reaction product. The recovery percentage was 99.3%.

Example 11

The extraction of a reaction product was effected by following the procedure of Example 2 while changing the temperature of the reaction product at the time of extraction to 180° C. The time required for the extraction was 2 minutes. The recovery percentage was 99.6%.

Comparative Example 3

The extraction of a reaction product was effected by following the procedure of Example 7 while stopping the stirring after completion of the reaction and changing the temperature of the reaction product at the time of extraction to 260° C. In this operation, only part of the reaction product could be extracted. The recovery percentage was 50%.

Comparative Example 4

The extraction of a reaction product was effected by following the procedure of Example 7 while stopping the stirring after completion of the reaction and changing the temperature of the reaction product at the time of extraction to 15° C. In this operation, the reaction product was hardly extracted.

What is claimed is:

1. A method for the production of an aromatic fluorine compound by the halogen exchange reaction of an aromatic chlorine compound with a fluorinating agent in a reaction vessel, characterized by extracting the aromatic fluorine compound obtained by the halogen exchange reaction from the reaction vessel at a temperature in the range of 50–230° C.

2. A method according to claim 1, wherein said adjustment of the reaction product to a temperature in the range of 50–230° C. is performed while the reaction product is kept stirred with stirring power per unit volume of the reaction product in the range of 0.1–10 kw/m$^3$.

3. A method according to claim 1, wherein the stirring in the reaction vessel at the time of extraction is carried out with stirring power per unit volume of the reaction product in the range of 0.01–3.0 kw/m$^3$.

4. A method according to claim 1, wherein the extraction of said reaction product is carried out under pressure.

5. A method according to claim 4, wherein said pressure is exerted by forcing a gas into the reaction vessel.

6. A method according to claim 1, wherein said extraction of the reaction product is effected by sucking the reaction product.

7. A method according to claim 6, wherein said suction is effected by the use of a pump.

8. A method according to claim 1, wherein said aromatic chlorine compound is one member selected from the group consisting of 3,4,5,6-tetrachlorophthalonitrile, pentachlorobenzonitrile, and 2,6-dichlorobenzonitrile.

9. A method according to claim 2, wherein said aromatic chlorine compound is one member selected from the group consisting of 3,4,5,6-tetrachlorophthalonitrile, pentachlorobenzonitrile, and 2,6-dichlorobenzonitrile.

10. A method according to claim 3, wherein said aromatic chlorine compound is one member selected from the group consisting of 3,4,5,6-tetrachlorophthalonitrile, pentachlorobenzonitrile, and 2,6-dichlorobenzonitrile.

11. A method according to claim 4, wherein said aromatic chlorine compound is one member selected from the group consisting of 3,4,5,6-tetrachlorophthalonitrile, pentachlorobenzonitrile, and 2,6-dichlorobenzonitrile.

12. A method according to claim 5, wherein said aromatic chlorine compound is one member selected from the group consisting of 3,4,5,6-tetrachlorophthalonitrile, pentachlorobenzonitrile, and 2,6-dichlorobenzonitrile.

13. A method according to claim 6, wherein said aromatic chlorine compound is one member selected from the group consisting of 3,4,5,6-tetrachlorophthalonitrile, pentachlorobenzonitrile, and 2,6-dichlorobenzonitrile.

14. A method according to claim 7, wherein said aromatic chlorine compound is one member selected from the group consisting of 3,4,5,6-tetrachlorophthalonitrile, pentachlorobenzonitrile, and 2,6-dichlorobenzonitrile.

15. A method according to claim 1, wherein said reaction product is extracted in the state of slurry.

* * * * *

UNITED STATES PATENT AND TRADEMARK OFFICE
CERTIFICATE OF CORRECTION

PATENT NO. : 6,437,168 B1
DATED : August 20, 2002
INVENTOR(S) : Kouichi Hirota

It is certified that error appears in the above-identified patent and that said Letters Patent is hereby corrected as shown below:

Column 11,
Line 35, after "C" insert -- with constant stirring --.

Signed and Sealed this

Seventeenth Day of February, 2004

JON W. DUDAS
*Acting Director of the United States Patent and Trademark Office*